United States Patent
Sugiyama

(10) Patent No.: US 8,691,220 B2
(45) Date of Patent: Apr. 8, 2014

(54) POWDERY MALTED RICE EXTRACT COMPOSITION

(75) Inventor: Masanori Sugiyama, Hiroshima (JP)

(73) Assignee: Hiroshima University, Higashi-Hiroshima-shi (JP)

( * ) Notice: Subject to any disclaimer, the term of this patent is extended or adjusted under 35 U.S.C. 154(b) by 0 days.

(21) Appl. No.: 13/504,139

(22) PCT Filed: Oct. 25, 2010

(86) PCT No.: PCT/JP2010/068865
§ 371 (c)(1),
(2), (4) Date: Jun. 6, 2012

(87) PCT Pub. No.: WO2011/052542
PCT Pub. Date: May 5, 2011

(65) Prior Publication Data
US 2012/0263704 A1   Oct. 18, 2012

(30) Foreign Application Priority Data

Oct. 26, 2009 (JP) ................................. 2009-245641

(51) Int. Cl.
*C12P 1/04* (2006.01)
(52) U.S. Cl.
USPC ........................................................ 424/115
(58) Field of Classification Search
USPC .......................................... 424/115; 426/43
See application file for complete search history.

(56) References Cited

U.S. PATENT DOCUMENTS

2002/0012985 A1   1/2002   Takebe et al.

FOREIGN PATENT DOCUMENTS

| JP | 3 130071 | | 6/1991 |
|---|---|---|---|
| JP | 3 172171 | | 7/1991 |
| JP | 5 15366 | | 1/1993 |
| JP | 2835548 | | 10/1998 |
| JP | 2000 342247 | | 12/2000 |
| JP | 2001 89354 | | 4/2001 |
| JP | 2001089354 A | * | 4/2001 |
| JP | 2005 82562 | | 3/2005 |
| JP | 2006 62984 | | 3/2006 |
| JP | 2007 153813 | | 6/2007 |
| JP | 2007/153813 A | * | 6/2007 |
| JP | 2007153813 A | * | 6/2007 |
| JP | 2008 247888 | | 10/2008 |
| JP | 2008247888 A | * | 10/2008 |
| WO | 99 10473 | | 3/1999 |

OTHER PUBLICATIONS

International Search Report Issued Dec. 21, 2010 in PCT/JP10/68865 Filed Oct. 25, 2010.

* cited by examiner

*Primary Examiner* — Susan Hanley
*Assistant Examiner* — Damon B Bowe
(74) *Attorney, Agent, or Firm* — Oblon, Spivak, McClelland, Maier & Neustadt, L.L.P.

(57) ABSTRACT

Disclosed are an agent for promoting proliferation of lactic acid bacteria, a preservative, and others, all of which do not deteriorate the flavor of food products. Specifically disclosed is a powdery malted rice extract composition obtained by inoculating lactic acid bacteria in a liquid prepared from a water extract of malted rice so that its Brix degree is 0.01 to 10, culturing the bacteria in the liquid, followed by drying the resulting culture.

18 Claims, 9 Drawing Sheets

POWDERY MALTED RICE EXTRACT COMPOSITION

This application is a National Stage of PCT/JP10/068,865 filed Oct. 25, 2010 and claims the benefit of JP 2009-245641 filed Oct. 26, 2009.

FIELD OF THE INVENTION

The present invention relates to a powdery malted rice extract composition, and an agent for promoting proliferation of plant-derived lactic acid bacteria and a preservative which are prepared using the powdery malted rice extract composition, and a method for producing a fermented food product using the powdery malted rice extract composition.

BACKGROUND OF THE INVENTION

Lactic acid bacteria are a generic term for microorganisms which commonly produce lactic acid by fermentation, and they play an important role in improving the flavor, texture, and nutritional value of a food product, imparting a preservative quality to a food product, and so on. Moreover, various physiological effects of lactic acid bacteria such as intestinal flora-improving effects and intestinal function-regulating actions brought about by ingestion of live lactic acid bacteria have been revealed, and research and development of food products, health-promoting food products, pharmaceutical products, and the like utilizing these physiological actions exerted by lactic acid bacteria have been conducted.

Further, plant-derived lactic acid bacteria, which play a major role in traditional fermented food products such as miso (fermented soybean paste) and Japanese pickles, are considered to be strong lactic acid bacteria which can survive in a condition of poor nutrient balance, and are rapidly gaining attention. However, compared to animal-derived lactic acid bacteria, plant-derived lactic acid bacteria have particularly low proliferation ability in milk, which has limited the utilization of plant-derived lactic acid bacteria in milk products.

Thus, if the promoted proliferation of plant-derived lactic acid bacteria, increased bacterial concentration, reduced fermentation time, and the like, can be successfully achieved in lactic acid fermentation in which plant-derived lactic acid bacteria is employed, then it will bring tremendous industrial utility value.

So far, it has been reported that sake lees and sake lees extracts or enzymatic degradation products of sake lees (refer to Patent documents 1 to 3), distillation residue liquids of shochu made from barley (Shochu is Japanese distilled spirit) (refer to Patent Document 4), wort fermentation products (refer to Patent Document 5), malted soybean fermentation products (refer to Patent Document 6), and the like have proliferation promoting actions on lactic acid bacteria.

However, it has not been revealed what kind of components of sake lees and distillation residue liquids of shochu can exhibit proliferation promoting actions on lactic acid bacteria. There is also a problem that sake lees impairs the flavor, appearance, and color tone of a fermented food product, which is the end product, due to its peculiar smell and color.

Meanwhile, malted rice, which is obtained by allowing koji mold (certain *Aspergillus* species) to grow on rice, is known to have a hypotensive action (refer to Patent Document 7), while water extracts of malted rice are known to have a moisturizing action (refer to Patent Document 8).

However, it has not been known that water extracts of malted rice exhibit proliferation promoting actions on plant-derived lactic acid bacteria and antibacterial activity against bacteria other than lactic acid bacteria.

PRIOR ART DOCUMENT

Patent Document

[Patent Document 1] JP-A-3-172171
[Patent Document 2] JP-A-5-15366
[Patent Document 3] JP-B-2835548
[Patent Document 4] JP-A-2000-342247
[Patent Document 5] JP-A-03-130071
[Patent Document 6] International Publication No. WO 99/10473
[Patent Document 7] JP-A-2008-247888
[Patent Document 8] JP-A-2001-89354

SUMMARY OF THE INVENTION

Problem to be Solved by the Invention

The present invention relates to provision of an easily handleable powdery malted rice extract composition which does not impair the flavor of a food product, and an agent for promoting proliferation of plant-derived lactic acid bacteria and a preservative which are prepared using the powdery malted rice extract composition, and a method for producing a fermented food product using the powdery malted rice extract composition.

Solution to Problem

Although powderization of a water extract of malted rice has been difficult, the present inventor has found that it is successfully powderized by culturing lactic acid bacteria in it. The present inventor has further found that the resulting powdery malted rice extract composition has excellent proliferation promoting actions on plant-derived lactic acid bacteria while exhibiting proliferation inhibiting actions on contaminants, and thus is useful not only as an agent for promoting proliferation of plant-derived lactic acid bacteria in the production of fermented food products but also as a preservative in cosmetics or food products (hereinbelow, may also be referred to as "cosmetics and the like").

That is, the present invention relates to the inventions according to the following 1) to 10).
1) A powdery malted rice extract composition obtained by inoculating lactic acid bacteria in a liquid prepared from a water extract of malted rice so that its Brix degree is 0.01 to 10, culturing the bacteria in the liquid, followed by drying the resulting culture.
2) The powdery malted rice extract composition according to the aforementioned 1), wherein the malted rice is a culture product of yellow koji mold.
3) An agent for promoting proliferation of plant-derived lactic acid bacteria containing the powdery malted rice extract composition according to the aforementioned 1) or 2).
4) A preservative containing the powdery malted rice extract composition according to the aforementioned 1) or 2).
5) The preservative according to the aforementioned 4), which is used by mixing it in a cosmetic.
6) A method for producing a fermented food product, including fermenting milk, fruit juice, or plant juice using plant-derived lactic acid bacteria in the presence of the powdery malted rice extract composition according to the aforementioned 1) or 2).

7) A fermented milk produced by fermenting milk using plant-derived lactic acid bacteria in the presence of the powdery malted rice extract composition according to the aforementioned 1) or 2).

8) A method for producing a powdery malted rice extract composition, including inoculating lactic acid bacteria in a liquid prepared from a water extract of malted rice so that its Brix degree is 0.01 to 10, culturing the bacteria in the liquid, followed by drying the resulting culture.

9) A method for promoting proliferation of plant-derived lactic acid bacteria, using the powdery malted rice extract composition according to the aforementioned 1) or 2).

10) A method for preserving a cosmetic or food product from decay, using the powdery malted rice extract composition according to the aforementioned 1) or 2) in a cosmetic or food product.

Effects of Invention

The use of the powdery malted rice extract composition of the present invention or an agent for promoting proliferation of plant-derived lactic acid bacteria containing the powdery malted rice extract composition makes it to promote proliferation of plant-derived lactic acid bacteria and efficiently produce a flavorful fermented food product, particularly, solid type fermented milk, which is usually difficult to produce by fermentation using plant-derived lactic acid bacteria, in a short time. Moreover, because this powdery malted rice extract composition can be stored for a long time and handled easily in the form of powder, it is also excellent in terms of operating efficiency and cost of the production of fermented food products. Further, because the powdery malted rice extract composition exhibits antibacterial actions against harmful bacteria such as *Staphylococcus aureus, enterococci*, and *E. coli*, it also functions as a preservative, and incorporation of the powdery malted rice extract composition into a cosmetic and the like prevents bacterial contamination, thereby increasing the preservative quality and stability of the cosmetic and the like.

DESCRIPTION OF EMBODIMENTS

Figure 1:
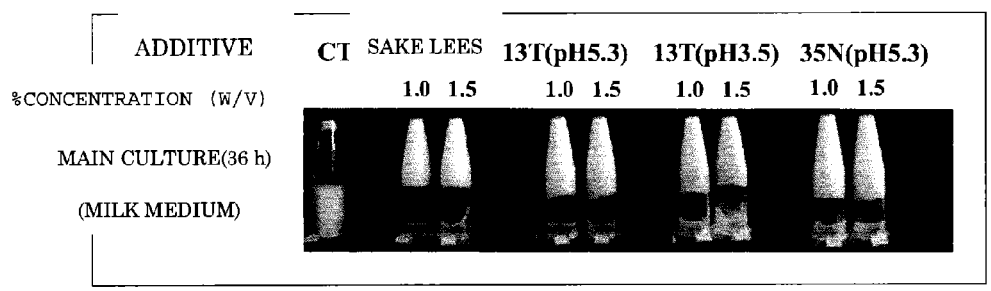
FIG. 1 is a photograph showing the solidified state of fermented milk after culturing in a milk medium containing the powdery malted rice extract composition or sake lees powder.

In the production of the powdery malted rice extract composition of the present invention, the water extract of malted rice to be used as the raw material is normally an aqueous solution of a high concentration of glucose (for example, 20% (m/v) or more). However, the concentration is not limited thereto, and an aqueous solution derived from the water extract of malted rice having a Brix degree of 5 to 40, particularly 15 to 35 is preferred.

Here, the Brix degree normally indicates the unit of the concentration of a sucrose solution and refers to the number of grams of sucrose in 100 g of a sucrose solution at 20° C. However, in the present invention, the Brix degree refers to the sucrose equivalent of a value obtained by measuring a filtered sample (20° C.) with a refractive saccharometer.

The aforementioned water extract of malted rice is obtained by extracting malted rice by adding water, and this encompasses suspending malted rice in water, allowing malted rice to absorb a large amount of water, and the like. The water extract contains a liquefying and saccharifying enzyme (starch hydrolase) produced by koji mold, a low molecular weight substance derived from rice, and the like. Further, the liquefying and saccharifying enzyme degrades rice, which serves as a substrate, into a low molecular weight substance by a treatment under the condition of specific temperature for a specific length of time, thereby producing an aqueous solution containing a high concentration of glucose, other monosaccharides and oligosaccharides, and the like, i.e., a liquefied and saccharified solution. The liquefied and saccharified solution from which the remnants (insoluble matters) are filtered off may also be called a koji syrup (for example, when the koji mold is *A. oryzae*, it is called a yellow koji syrup, and when the koji mold is *A. kawachii*, it is called a white koji syrup, etc.).

For example, extraction of malted rice with water may be performed by adding 1 to 500 g (preferably 200 to 400 g) of malted rice (dry equivalent) to 1 L of an aqueous solution, and leaving the resulting solution to stand at 30 to 70° C. (preferably 50 to 65° C.) for 1 minute to 48 hours (preferably 18 to 30 hours). In this process, rice or heat-treated products of rice may be added, and stirring, shaking, and the like may be performed as needed.

Insoluble matters present in the water extract (for example, unliquefied rice, mold cells, and enzymes) may be removed by centrifugation, filtration, and the like, and it may be possible to kill koji mold or inactivate the enzymes by heating and the like.

In the present invention, "malted rice" means a koji mold culture product of rice, which is obtained by adding koji mold to rice, a heat-treated product of rice, or a suspension of rice or a heat-treated product of rice and culturing the koji mold. This malted rice culture product is commonly called koji (may also be called yellow koji, white koji, etc. depending on the kind of mold), which is normally commercially available as a dried product.

Culture of koji mold may be carried out by a method routinely employed in the production of sake (Japanese alcoholic beverage) and shochu; however, for example, koji mold may be inoculated and cultured in rice, a heat-treated product of rice, or a suspension of rice or a heat-treated product of rice, using these as a medium.

Examples of rice as a raw material of malted rice (koji) normally include unpolished rice, polished rice, rice bran, or a product obtained by physically processing (i.e., crushing and pulverizing) the above materials (such as rice powder). Among them, polished rice and rice powder, which have high starch content, are preferred.

The heat-treated product of rice is preferably steam-treated or heat moisture-treated rice since heat treatment of rice in the presence of water not only makes subsequent saccharification and liquefaction of rice easy but also kills microorganisms. Examples of the above-mentioned treatment include boiling polished rice and further making it into a paste, autoclaving an aqueous solution containing rice powder, and steam-treating the rice powder. These sterilized rice powder and steamed rice are more preferred as the raw materials for the production of koji.

The koji mold is not particularly limited as long as it is capable of saccharifying and liquefying rice, and *Aspergillus oryzae*, i.e., a yellow koji mold; *Aspergillus kawachii*, i.e., a white koji mold; *Aspergillus awamori*, i.e., a black koji mold; and *Aspergillus sojae*, i.e., a soy sauce koji mold, all of which are used in sake, shochu, miso, soy sauce, and the like, are preferred. Among them, particularly *Aspergillus oryzae*, i.e., a yellow koji mold, is preferred.

Koji mold may be used as a single species or a combination of two or more species if appropriate.

The powdery malted rice extract composition according to the present invention is produced by inoculating lactic acid bacteria in a liquid prepared from the water extract of malted rice so that its Brix degree is 0.01 to 10 (hereinbelow, may also be referred to as a "water extract solution"), culturing the bacteria in the liquid, followed by drying the resulting culture.

In inoculation of lactic acid bacteria, the water extract of malted rice is prepared so that its sugar content is 0.01 to 10 by Brix degree. The Brix degree may be adjusted by dilution with water, concentration, and the like, and when the Brix degree of the raw material is within the above range, adjustment is not particularly needed.

When the Brix degree is 0.01 to 10, culture of lactic acid bacteria is generally favorably carried out. In view of achieving better culture of lactic acid bacteria, the Brix degree is preferably 0.05 to 5, more preferably 0.1 to 4, and further, in terms of operating efficiency, the Brix degree is preferably 0.5 to 3.

In that case, the solid content of the water extract solution is preferably 0.5 to 4% by mass, more preferably 1 to 3% by mass. It should be noted that the solid content (evaporation residue) refers to the content excluding evaporable components such as water, and is calculated by [(mass after drying/mass before drying)×100] and expressed as % by mass.

Subsequently, lactic acid bacteria are inoculated and cultured in a solution containing the water extract of malted rice and having prepared Brix degree.

Lactic acid bacteria may be cultured in accordance with a common culture method of lactic acid bacteria, for example, lactic acid bacteria may be inoculated in the order of $10^8$ to $10^9$/mL (preferably, $10^9$ or more/mL) in the aforementioned water extract solution and cultured at 30 to 45° C. (preferably, 30 to 40° C.) for 1 to 72 hours (preferably, 16 to 32 hours). At this time, it is preferable to adjust the medium pH to 5 to 8, more preferable to 5 to 6 with the addition of a pH adjuster such as sodium citrate since in that way the number of lactic acid bacteria is successfully increased to the desired concentration in the end product.

A starter may also be used in inoculation.

No particular limitation is imposed on lactic acid bacteria used, and examples thereof include bacteria belonging to the genus *Lactobacillus*, bacteria belonging to the genus *Streptococcus*, bacteria belonging to the genus *Leuconostoc*, bacteria belonging to the genus *Pediococcus*, bacteria belonging to the genus *Bacillus*, bacteria belonging to the genus *Lactococcus*, bacteria belonging to the genus *Enterococcus*, bacteria belonging to the genus *Tetragenococcus*, and bacteria belonging to the genus *Bifidobacterium*. No particular limitation is imposed on the source of isolation such as an animal, a plant, and the like, and either animal-derived lactic acid bacteria or plant-derived lactic acid bacteria may be used, of which plant-derived lactic acid bacteria are preferred. Examples of the plant-derived lactic acid bacteria include those described below, and among them bacteria belonging to the genus *Lactobacillus* are preferred, of which *Lactobacillus plantarum* is more preferred.

Lactic acid bacteria may be used as a single species or a combination of two or more species if appropriate.

Upon completion of culture, the culture liquid is dried to give the powdery malted rice extract composition of the present invention.

As the drying means, commonly employed drying means may be used, and examples thereof include freeze drying, spray drying, and hot air or cold air drying. Among them, freeze drying and cold air drying are preferred in view of the inhibition of degradation of the components, whereas spray drying is preferred in terms of operating efficiency.

It may be possible to perform sterilization treatment by heating or the like, or remove insoluble matters by filtration, centrifugation or the like, before drying as needed, to kill lactic acid bacteria (in some cases, lactic acid bacteria and koji mold) or remove insoluble matters contained in the culture liquid. However, when a highly health-promoting strain is used as the plant-derived lactic acid bacteria, it is also beneficial to dry the resulting culture product without performing sterilization treatment or insoluble matter-removal treatment because the resulting powdery malted rice extract composition can attain not only a proliferation promoting action on lactic acid bacteria but also an effect exerted by beneficial functional molecules derived from the lactic acid bacteria.

Sterilization may be performed by a sterilization method commonly employed in food manufacturing such as low-temperature heat sterilization, high-temperature heat sterilization, and autoclave sterilization, of which autoclave sterilization is preferably employed in view of operating efficiency.

Since conventional water extracts of malted rice are a liquid with high sugar content, they were hard to powderize because they turned into a viscous liquid when subjected to drying treatment. Consequently, their large volume caused inconvenience in storage and distribution, and due to the water content, the components were likely to be modified by various bacteria and enzymes as well as temperature, light, and other factors. Moreover, when they were prepared as a viscous liquid, the solubility in water was deteriorated. For these reasons, conventional water extracts of malted rice were difficult to handle in terms of both the industrial and commercial aspects. However, the use of the aforementioned method of the present invention enables powderization of the water extract of malted rice, and thereby solving the aforementioned problems while increasing the industrial and commercial convenience and value of the water extract of malted rice.

Further, as will be demonstrated in Examples later, when plant-derived lactic acid bacteria are cultured in milk in the presence of the powdery malted rice extract composition of the present invention, lactic acid fermentation promptly proceeds. Accordingly, the powdery malted rice extract composition can be used as an agent for promoting proliferation of lactic acid bacteria in lactic acid fermentation.

Compared to animal-derived lactic acid bacteria isolated from an animal source such as animal meat and milk, plant-derived lactic acid bacteria normally have lower proliferation ability, which makes it difficult to produce solid type yogurt with them. However, the use of the powdery malted rice extract composition of the present invention enables the production of solid type yogurt.

Further, the powdery malted rice extract composition of the present invention has proliferation inhibiting actions on harmful bacteria which cause food poisoning and infectious diseases such as Streptococcus aureus, Enterococcus faecalis, Escherichia coli, Bacillus subtilis, Bacillus cereus, Staphylococcus epidermidis, and Listeria monocytogenes. While sake lees and sake lees extracts are also known to have proliferation promoting actions on lactic acid bacteria, they simultaneously activate the proliferation of Streptococcus aureus and Streptococcus mutans. Accordingly, in light of the application to food products and the like, the powdery malted rice extract composition of the present invention is assumed to be more useful than sake lees.

Further, the powdery malted rice extract composition of the present invention having proliferation inhibiting actions on harmful bacteria such as Streptococcus aureus functions as a highly safe preservative derived from natural food products, and is mixed in cosmetics and the like, thereby exerting an effect of increasing the preservative quality and safety of the cosmetics and the like. For example, since cosmetics such as bottled skin toning solutions and lotions are poured into a hand before application to the skin, the remaining solutions or lotions may be contaminated by germs attached to the hand via the bottle opening. In light of this, bacterial contamination of these products can be prevented by adding highly safe natural preservatives in advance.

The agent for promoting proliferation of plant-derived lactic acid bacteria of the present invention can be applied to plant-derived lactic acid bacteria, and examples of plant-derived lactic acid bacteria isolated from a plant source such as grains, vegetables, fruits, flowers, and medicinal plants include bacteria belonging to the genus Lactobacillus such as Lactobacillus plantarum, Lactobacillus hilgardii, Lactobacillus brevis, Lactobacillus curvatus, and Lactobacillus fermentum; bacteria belonging to the genus Leuconostoc such as Leuconostoc mesenteroides; bacteria belonging to the genus Enterococcus such as Enterococcus mundtii and Enterococcus avium; bacteria belonging to the genus Tetragenococcus such as Tetragenococcus halophilus; bacteria belonging to the genus Pediococcus such as Pediococcus pentosaceus and Pediococcus acidilactici; and bacteria belonging to the genus Bacillus such as Bacillus coagulans.

Specific examples of the aforementioned plant-derived lactic acid bacteria include the Lactobacillus plantarum SN13T strain (NITE P-7), the Lactobacillus plantarum SN26T strain (NITE P-8), the Lactobacillus plantarum SN35N strain (NITE P-6), the Lactobacillus plantarum SN35M strain (NITE P-5), the Lactococcus lactis subsp. lactis SN26N strain (NITE P-9), the Enterococcus sp. SN21I strain (NITE P-11), the Enterococcus mundtii SN29N strain (NITE P-10) and the Enterococcus avium (NITE BP-142), the Lactobacillus plantarum JCM 1149 strain, the Lactobacillus plantarum JCM 8348 strain, the Lactobacillus plantarum IFO3070 strain (JCM 1057 strain), and the Lactobacillus hilgardii NBRC15886.

From the viewpoint of favorable proliferation in the presence of the powdery malted rice extract composition of the present invention, among the above plant-derived lactic acid bacteria, bacteria belonging to the genus Lactobacillus are preferred, of which Lactobacillus plantarum is more preferred, and the Lactobacillus plantarum SN13T strain (NITE P-7) and the Lactobacillus plantarum SN35N strain (NITE P-6) are particularly preferred.

A fermented food product, which uses the powdery malted rice extract composition of the present invention as an agent for promoting proliferation of plant-derived lactic acid bacteria, can be produced by inoculating the aforementioned plant-derived lactic acid bacteria into the fermentation raw material in accordance with a known method in the presence of the powdery malted rice extract composition.

For example, the fermented food product can be produced by adding the powdery malted rice extract composition of the present invention to the fermentation raw material such as milk, vegetables, and fruits in such a way that the composition directly contacts the fermentation raw material, or adding the powdery malted rice extract composition in an amount of preferably 0.01 to 10% (m/v), more preferably 0.01 to 5% (m/v), and even more preferably 0.5 to 2% (m/v) per liter of medium, inoculating and culturing lactic acid bacteria in the medium at 25 to 45° C. for 10 to 80 hours.

Hereinbelow, the production of fermented milk will be described as an example. In the production of fermented milk, it is preferred that a medium contains 0.1 to 20% (m/v) of skim milk or milk (dry equivalent) per liter.

For example, when yogurt fermentation is carried out, an aqueous solution in which the content of non-fat milk solid mainly made of milk is adjusted to a concentration of 8.0% or more (m/v) is subjected to heat sterilization at 65 to 130° C. for 1 second to 30 minutes, and then cooled to a temperature of 30 to 45° C., whereby a milk-containing liquid medium (hereinbelow, may also be referred to as a "milk liquid medium") is prepared. Into the milk liquid medium thus prepared, the powdery malted rice extract composition of the present invention is added in an amount of 0.1 to 5% (m/v) per liter of medium, whereby a milk liquid medium containing the powdery malted rice extract composition is prepared. Subsequently, highly concentrated lactic acid bacteria, which are prepared as a starter, are inoculated into the medium thus prepared in an amount of 0.1 to 6% (m/v). After inoculation, fermentation is carried out at a temperature of 30 to 45° C. for 3 to 72 hours in the presence of the powdery malted rice extract composition of the present invention until the number of lactic acid bacteria reaches ten million/mL or more. Upon completion of fermentation, the resulting product is cooled to 10° C. or below, which is provided as yogurt.

For example, in the case of a fermented milk drink, milk (1% or more (m/v) as dry equivalent in the aqueous solution) or an aqueous solution prepared by blending the milk and other raw materials is subjected to heat sterilization at a temperature of 65 to 130° C. for 1 second to 30 minutes, and then cooled to 30 to 45° C. Subsequently, into the resulting solution, lactic acid bacteria are inoculated as a starter in an amount of 0.1 to 6% (m/v). After inoculation, fermentation is carried out at a temperature of 30 to 45° C. for 12 to 72 hours in the presence of the powdery malted rice extract composition of the present invention. Upon completion of fermentation, the resulting product is cooled, which is provided as a fermented milk drink. The resulting product may be provided directly as a drink, or diluted or sterilized. At this time, the content of the powdery koji mold culture composition of the present invention is preferably 0.1 to 2% (m/v) per liter of the aqueous solution into which the raw materials such as milk have been blended.

In the production of the aforementioned fermented milk, besides the raw material milk, raw materials which are commonly employed in the production of fermented drinks such as gelatin, agar, sugars, fragrances, flesh of fruit, nitrogen sources, pH adjusters, and other lactic acid bacteria proliferation-promoting components can be added. For example, sugars such as sucrose, glucose, fructose, palatinose, and trehalose, sugar alcohols such as sorbitol, xylitol, erythritol, and reduced sugar syrup, high intensity sweeteners such as aspartame and acesulfame K, emulsifiers such as a sucrose fatty acid ester, a glycerin fatty acid ester, and lecithin, viscosity increasing agents such as carrageenan, xanthan gum, and guar gum, acidifiers such as citric acid, lactic acid, and malic acid, fruit juice such as lemon juice, orange juice, pineapple juice, kiwi juice, and pear juice, and in addition, vitamins and minerals such as calcium, iron, manganese, and zinc, and further, crude drugs such as licorice, cinnamon, and ginger, or food additives such as herbs, sodium glutamate, Gardenia pigment, silicone, and phosphate salts may be added.

Examples of the fermentation raw material milk include animal milk such as cow milk, goat milk, and sheep milk, of which cow milk is particularly preferred. The milk may be either unsterilized milk or sterilized milk, or may also be concentrated milk or condensed milk prepared from above milks, skimmed or partially skimmed milk prepared from above milks, or powdery milk obtained by drying and powderizing the above milks.

In a fermented product (fermented milk) produced by using the agent for promoting proliferation of lactic acid bacteria of the present invention obtained as above, lactic acid fermentation proceeds promptly as will be demonstrated in Examples later. That is, even when plant-derived lactic acid bacteria are used, with which normally the production of solid type fermented milk is assumed to be difficult due to their extremely low proliferation ability, the fermented milk promptly becomes solidified (solidified fermented milk).

According to the method for producing fermented milk of the present invention, the proliferation ability of plant-derived lactic acid bacteria can be adjusted as appropriate, and fermented milk in any form such as a plain type, a soft type, a drink type, a solid (hard) type, or a frozen type fermented milk can be produced.

When the powdery malted rice extract composition of the present invention is used as a preservative, the powdery malted rice extract composition can be used as is or may also be mixed with other additives and prepared into a flaky form, a granular form, and the like.

As to the usage of the preservative, it may be added to food products, cosmetics, and the like by an appropriate method, and no particular limitation is imposed on the method of adding.

Examples of a food product to which the preservative of the present invention is applied include various food products, for example drinks such as fruit juice or vegetable juice drinks, carbonated drinks, tea-based drinks, alcoholic drinks, and soft drinks, jelly food products, various snacks, baked confectioneries, cakes, chocolate, jam, bread, gum, candy, soups, pickles, and food boiled in soy sauce).

For the cosmetics, the preservative of the present invention is applied to any form of cosmetic, for example a basic cosmetic such as a cream, an emulsion, a lotion, a face wash, and a facial mask, a make-up cosmetic such as a lipstick and a foundation, a cleansing agent such as a body soap and a soap, a hair care product such as a hair product including a hair tonic, a hair liquid, a hair setting lotion, a hair blowing agent, a hair cream, and a hair coat and a toiletry product for hair such as a shampoo, a conditioner, and a hair treatment agent.

The amount of the powdery malted rice extract composition added to the food products and cosmetics varies depending on the kind of the food product or cosmetic, and the amount to be added may be determined according to the purpose of addition. The malted rice extract composition may be added, in terms of the solid content, normally in an amount of 0.5 to 10 parts by mass, preferably 1 to 5 parts by mass, with respect to 100 parts by mass of the food product or cosmetic.

EXAMPLES

Hereinbelow, the present invention will be described specifically with reference to Examples; however, the present invention is not limited to these Examples in any way.

Example 1

Preparation of the Water Extract of Malted Rice

<Bacteria Used>

A species of *Lactobacillus plantarum*, i.e., the *Lb. plantarum* SN13T strain or the *Lb. plantarum* SN35N strain was used.

The above strains have been deposited with The National Institute of Technology and Evaluation (Address: 2-5-8 Kazusakamatari, Kisarazu-shi, Chiba) as the *Lactobacillus plantarum* SN13T strain (NITE P-7) and *Lactobacillus plantarum* SN35N strain (NITE P-6) (Deposition date: Jul. 6, 2004).

<Preparation of a Rice Fermentation Extract>

To 350 g of dry koji (yellow koji mold: *Aspergillus oryzae*), 1 L of water was added to extract koji with water while allowing saccharification and liquefaction to proceed at 60° C. for 24 hours, whereby a crude water extract of malted rice was obtained. The crude water extract of malted rice was coarsely filtered, sterilized by autoclaving, and then subjected to microfiltration to give a water extract of malted rice (yellow koji syrup). The dry koji was in a powdery form, which was obtained from Yaegaki Bio-Industry, Inc.

The solid content was 21.6% by mass and the Brix degree was 24.6 in the water extract of malted rice (yellow koji syrup).

It should be noted that the solid content (evaporation residue) is a value expressed by the formula [(mass after drying/mass of yellow koji syrup)×100 (% by mass)], wherein the mass after drying is obtained by heating the koji syrup at 105° C., drying the syrup, and weighing the residual product.

The Brix degree refers to the sucrose equivalent of a value obtained by measuring a filtered sample (20° C.) with a refractive saccharometer.

<Preparation of the Powdery Malted Rice Extract Composition 1>

A liquid preparation obtained by diluting the water extract of malted rice obtained as above 10-fold with water (Brix degree of 2.5, solid content of 2.2% by mass) was sterilized by autoclaving at 121° C. for 20 minutes to prepare a sterilized malted rice water extract solution.

Further, the sterilized malted rice water extract solution having an unadjusted pH (pH 3.5) was used as a medium.

Into this medium, the *Lb. plantarum* SN13T bacterial strain was inoculated and cultured at 37° C. for 24 hours (generally, $10^9$ or more/mL), and the resulting culture liquid was sterilized by autoclaving at 121° C. for 20 minutes. Subsequently, the resulting sterilized lactic acid bacteria culture liquid was freeze-dried to give a powderized malted rice extract composition 1 (hereinbelow, may also be referred to as the "powdery malted rice extract composition 1" or "13T (pH 3.5)").

Lactic acid bacteria were inoculated into the above-described sterilized malted rice water extract solution having an unadjusted pH and the resulting solution was immediately sterilized by autoclaving, followed by freeze-drying; however, the resulting product could not be powderized but remained as a viscous liquid.

<Preparation of the Powdery Malted Rice Extract Composition 2>

Except for adjusting the pH of the aforementioned medium before inoculation of bacteria to 5.3 with sodium citrate, lactic acid bacteria were cultured in the same manner as the aforementioned <preparation of the powdery malted rice extract composition 1>, and freeze-dried to give a powderized rice fermentation product 2 (hereinbelow, may also be referred to as the "powdery malted rice extract composition 2" or "13T (pH 5.3)").

<Preparation of the Malted Rice Extract Composition 3>

Except for changing the bacteria to be inoculated from the *Lb. plantarum* SN13T bacterial strain to the *Lb. plantarum* SN35N bacterial strain, lactic acid bacteria were cultured in the same manner as the aforementioned <preparation of the powdery malted rice extract composition 2>, and freeze-dried to give a powderized powdery malted rice extract composition 3 (hereinbelow, may also be referred to as the "powdery malted rice extract composition 3" or "35N (pH 5.3)").

<Preparation of the Sake Lees Powder>

Commercially available sake lees was spray-dried to give a sake lees powder.

Example 2

Lactic Acid Bacteria Proliferation Promotion Test (1) and Fermented Milk Solidification Test <Preculture (Preparation of a Starter)>

The aforementioned *Lb. plantarum* SN35N strain was cultured in a culture medium for lactic acid bacteria (MRS medium) at 37° C. for 24 hours. After culturing, the bacteria were washed with a phosphate buffer (pH 7.0) and suspended in sterilized water to prepare a *Lb. plantarum* SN35N strain starter.

<Main Culture (Use of a Skimmed Milk Powder Medium)>

(1) Into an aqueous solution of 13% skimmed milk powder (hereinbelow, may also be referred to as a "milk medium"), the powdery malted rice extract composition 1 produced in Example 1 as described above was added in an amount of 1.0 or 1.5% (mass/volume) (hereinbelow, "% (mass/volume)" is abbreviated as "% (m/v)") to prepare milk media having respective concentrations of the powdery malted rice extract composition 1. A milk medium to which no powdery malted rice extract composition was added was used as a control (may also be referred to as "CT").

Further, except for changing the "powdery malted rice extract composition 1" to the "sake lees powder", milk media having respective concentrations of the sake lees powder were prepared in the same manner as above.

(2) Except for changing the "powdery malted rice extract composition 1" to the "powdery malted rice extract composition 2", milk media having respective concentrations of the powdery malted rice extract composition 2 were also prepared in the same manner as above.

(3) Except for changing the "powdery malted rice extract composition 1" to the "powdery malted rice extract composition 3", milk media having respective concentrations of the powdery malted rice extract composition 3 were also prepared in the same manner as above.

(4) The starter (*L. plantarum* SN35N strain) prepared as described above was added to each of the above-described milk media in an amount of 1% (v/v) and cultured at 37° C. for 36 hours.

As shown in FIG. 1, fermented milk was solidified in all of the media containing the powdery malted rice extract compositions 1 to 3, based on which the powdery malted rice extract composition of the present invention was found to have a proliferation promoting action on lactic acid bacteria. Here, fermented milk of plant-derived lactic acid bacteria was favorably solidified at a concentration of either 1.0% (m/v) or 1.5% (m/v), and solidification of the fermented milk was almost complete in 24 hours.

Further, comparing the sake lees powder and the powdery malted rice extract composition, even when the sake lees powder was added in an amount of 1.0% (m/v), peculiar odor of sake was noted, which impaired the flavor of the solidified fermented milk, whereas even when the powdery malted rice extract composition was added in an amount of 1.5% (m/v), there was no unpleasant odor, and the flavor, texture, appearance, etc. of the solidified fermented milk thus obtained were not impaired. From these results, the powdery malted rice extract composition of the present invention can be used for the production of solidified fermented milk in which plant-derived lactic acid bacteria is used.

Further, because the powdery malted rice extract composition per se is naturally free from unpleasant odor, it does not impair the flavor of a fermented food product even when it is added in an increased amount. Thus, the powdery malted rice extract composition of the present invention can be used in a wide range of fermented food products, and thus has high utility value.

To obtain the powdery malted rice extract composition, solidification was slightly faster in a pH-unadjusted medium (pH 3.5) than in a pH-adjusted medium (pH 5.3), but solidification of fermented milk favorably proceeded in a medium in both cases of pH 3.5 and 5.3. From these results, the pH of the lactic acid bacteria culture liquid in the production of the powdery malted rice extract composition of the present invention may be in a range of 3 to 6. However, at pH 3, milk might be solidified due to an additive effect with the acidity of the medium before lactic acid bacteria proliferates to the desired concentration. Given that it is an indispensable condition that at least ten million lactic acid bacteria are present per mL of fermented milk, the initial pH of the medium is preferably in a range of 5 to 6.

Although faster solidification was observed with the powdery malted rice extract composition 2 produced by culturing the *Lactobacillus plantarum* SN13T strain than with the powdery malted rice extract composition 3 produced by culturing the *Lactobacillus plantarum* SN35N strain, solidification of fermented milk favorably proceeded in both cases of the above powdery malted rice extract compositions. From these results, it was assumed that either animal-derived lactic acid bacteria or plant-derived lactic acid bacteria may be used as the lactic acid bacteria used in the production of the powdery malted rice extract composition of the present invention.

Example 3

Proliferation Promotion Test of Harmful Bacteria (1)

As the harmful bacteria, the *Staphylococcus aureus* (IFO 12732) strain was used.

The sake lees powder used as above and the powdery malted rice extract composition 1 (13T) or powdery malted rice extract composition 3 (35N) prepared in Example 1 were used as samples. The samples were each added to Luria Broth (LB) media (the product of Sigma-Aldrich Japan K.K.) in an amount of 0.750 (m/v) to prepare respective media. Then, the *Staphylococcus aureus* (IFO 12732) bacterial strain was inoculated into each medium and cultured at 37° C., and a bacterial turbidity was measured (OD 600 nm) every six hours. A medium containing none of the above substances (CT) was used as a control.

Figure 2:
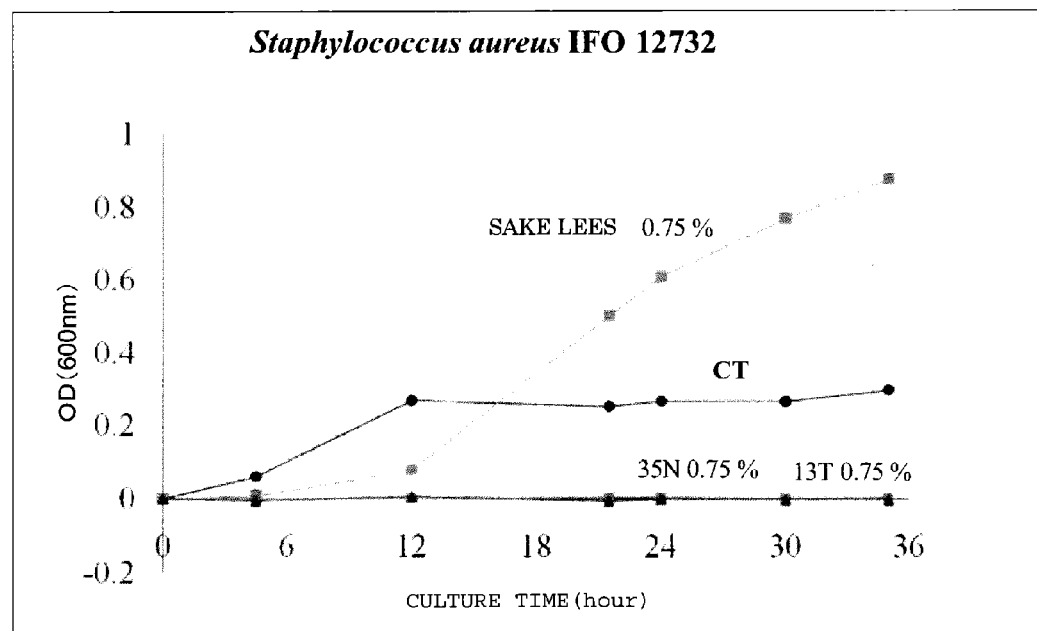
FIG. 2 is a graph showing the effect of sake lees and the powdery malted rice extract composition (13T and 35N) on the growth of *Staphylococcus aureus*.
Figure 3:
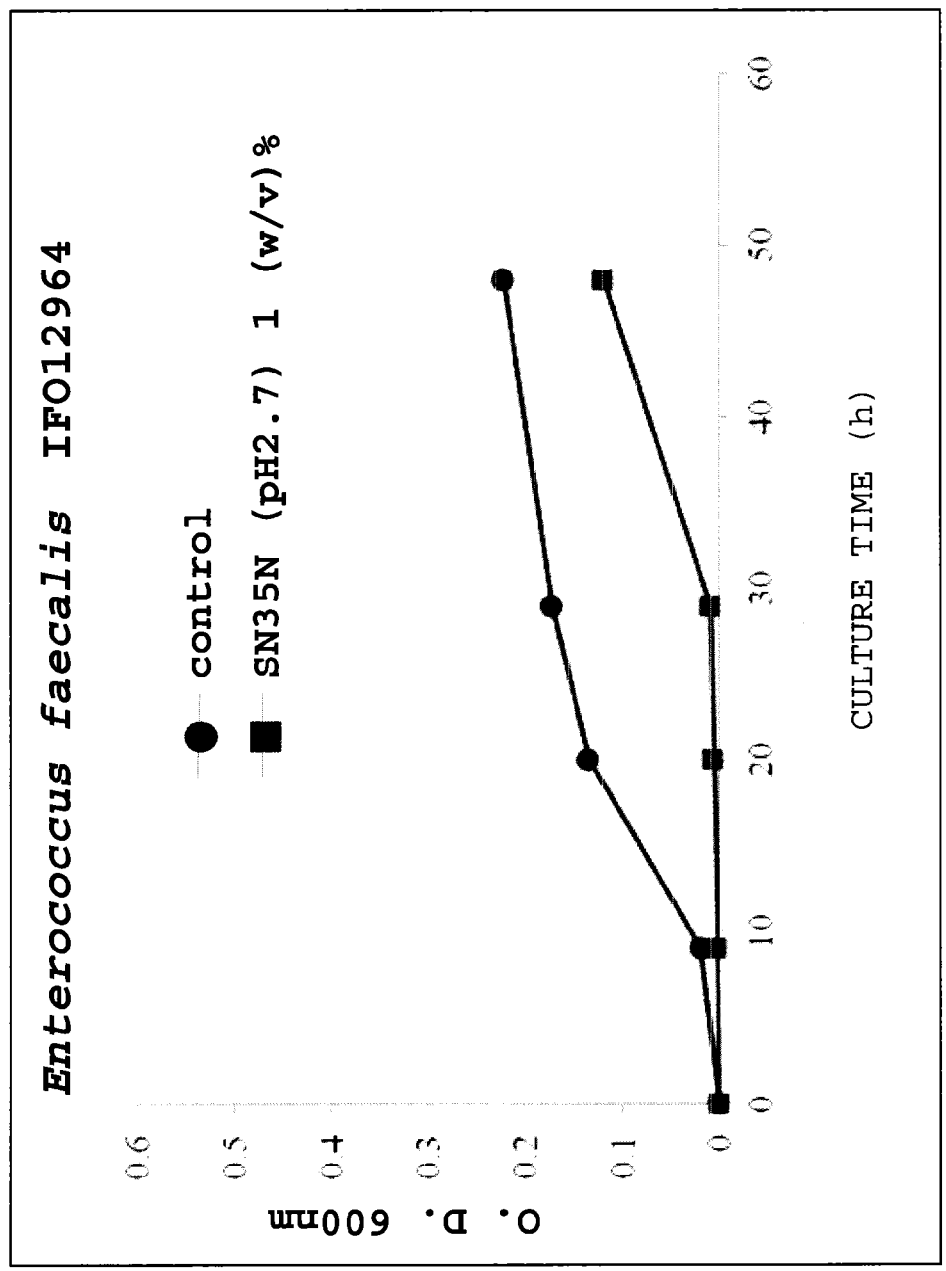
FIG. 3 is a graph showing the effect of the powdery malted rice extract composition (SN35N) on the growth of *Enterococcus faecalis*.
Figure 4:
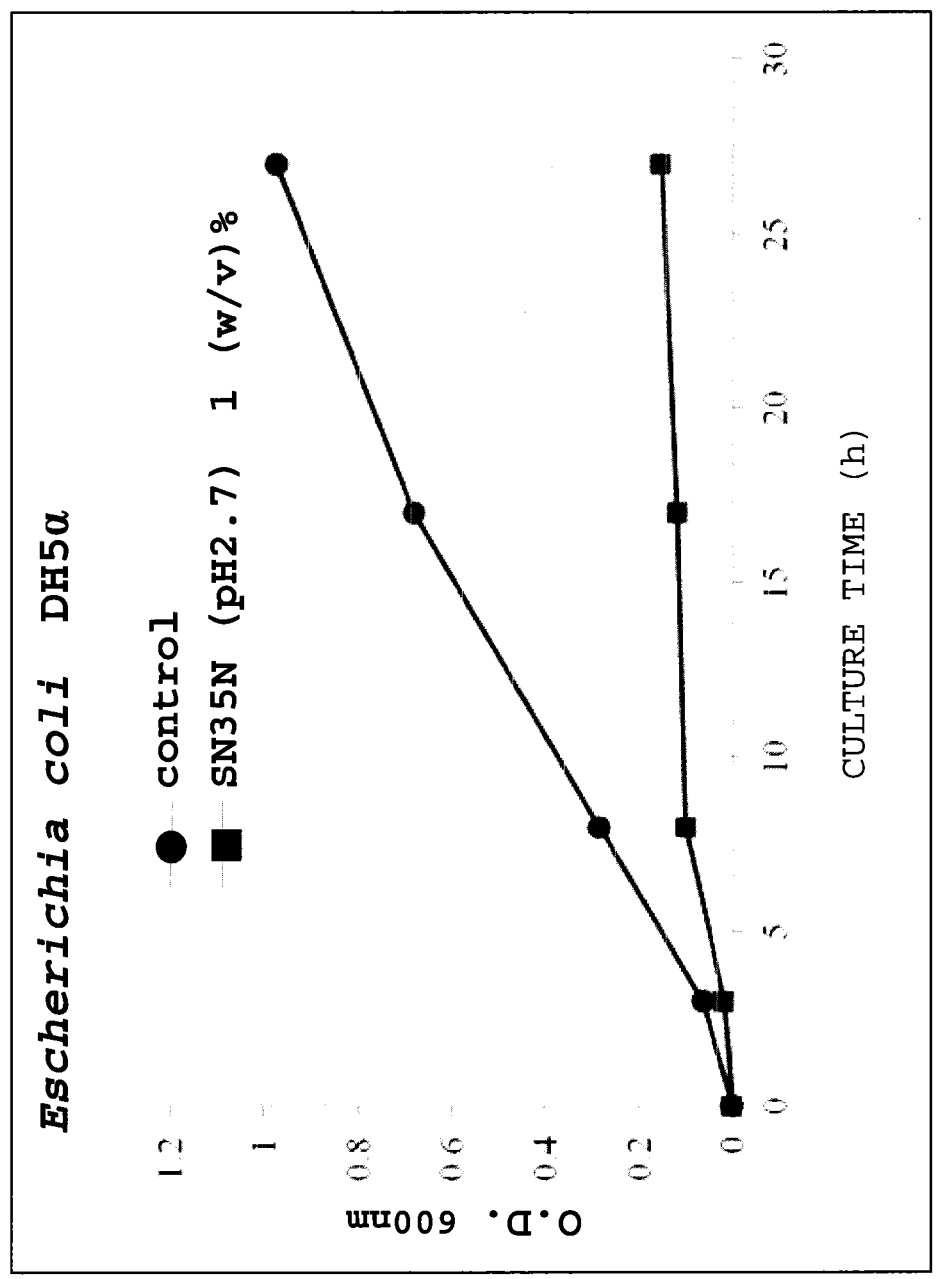
FIG. 4 is a graph showing the effect of the powdery malted rice extract composition (SN35N) on the growth of *Escherichia coli*.
Figure 5:
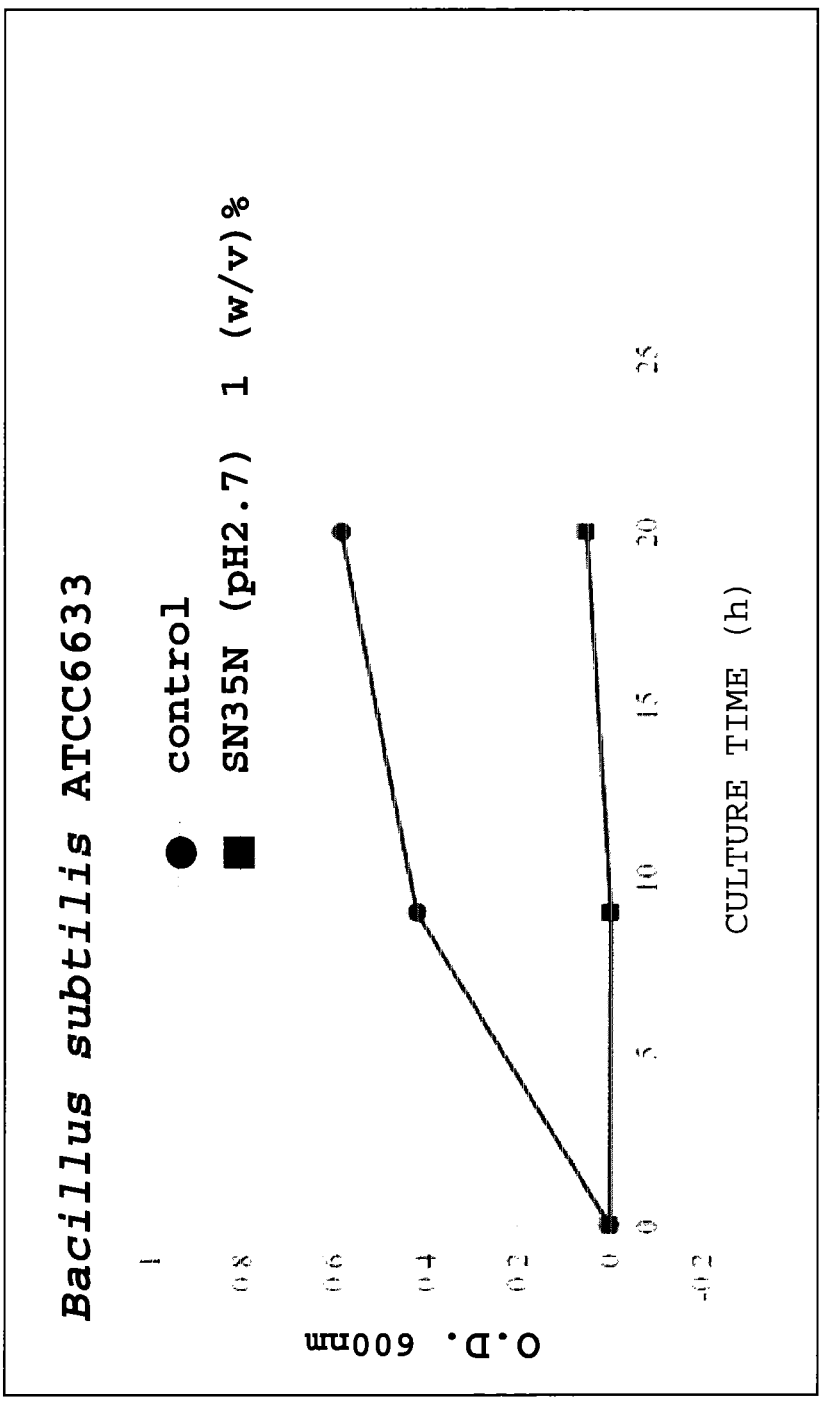
FIG. 5 is a graph showing the effect of the powdery malted rice extract composition (SN35N) on the growth of *Bacillus subtilis*.
Figure 6:
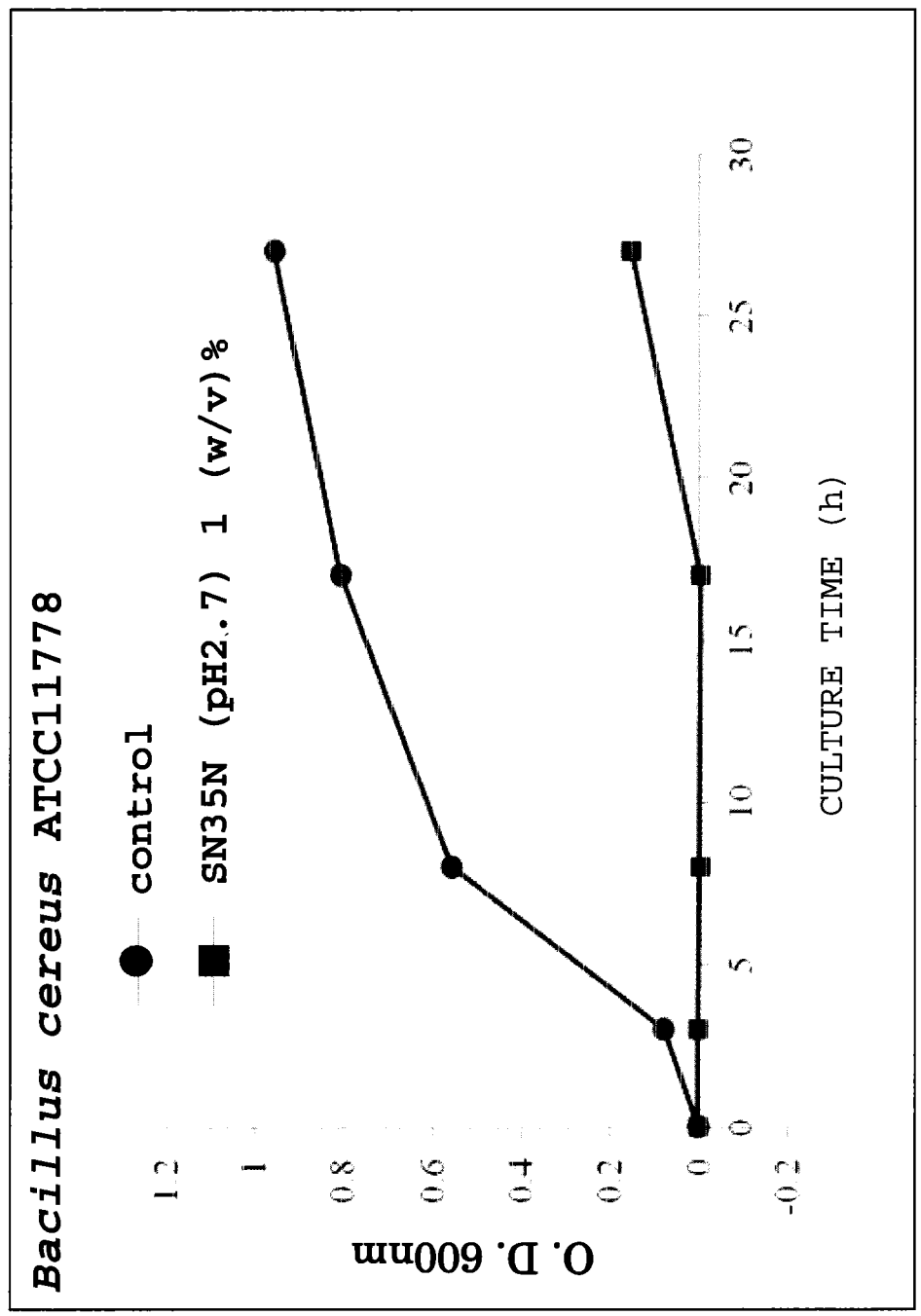
FIG. 6 is a graph showing the effect of the powdery malted rice extract composition (SN35N) on the growth of *Bacillus cereus*.
Figure 7:
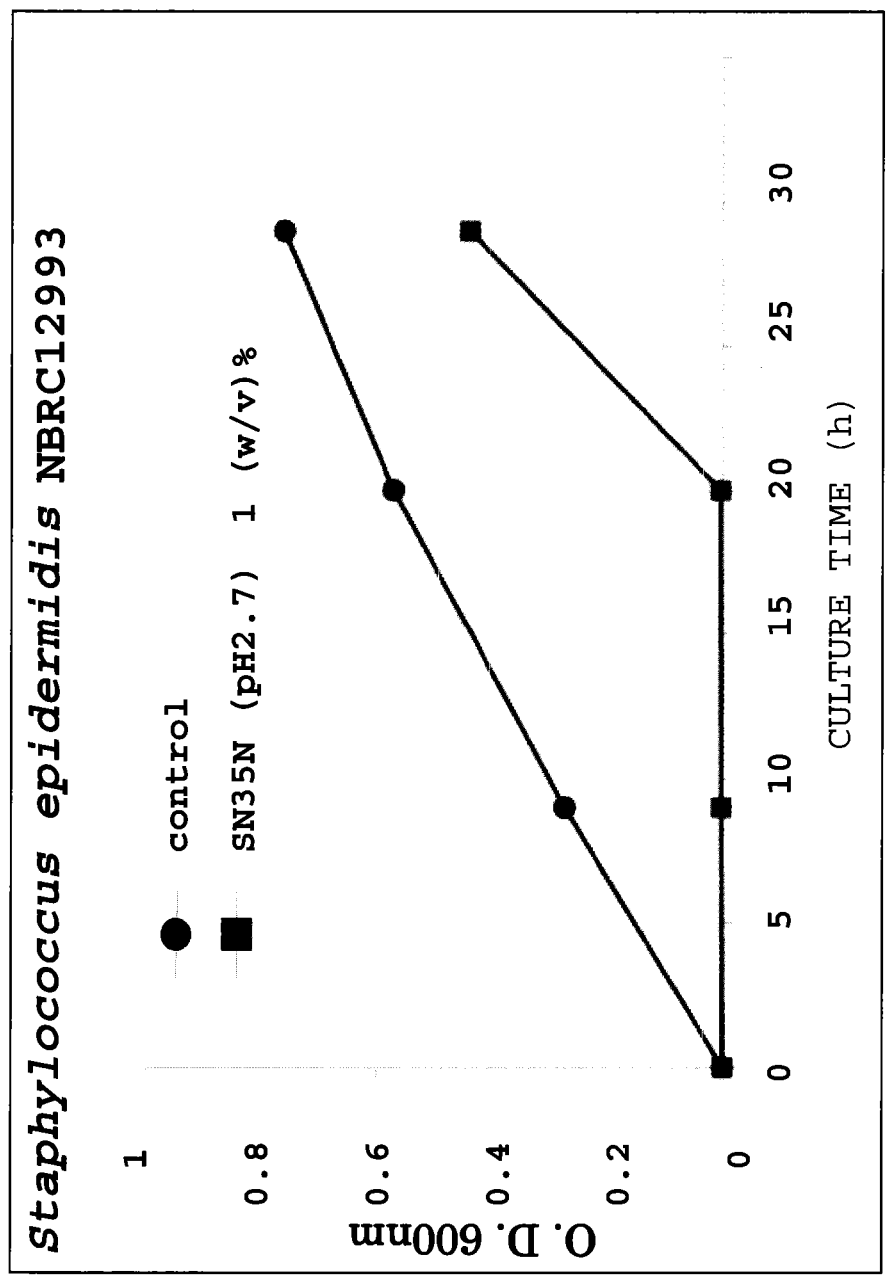
FIG. 7 is a graph showing the effect of the powdery malted rice extract composition (SN35N) on the growth of *Staphylococcus epidermidis*.
Figure 8:
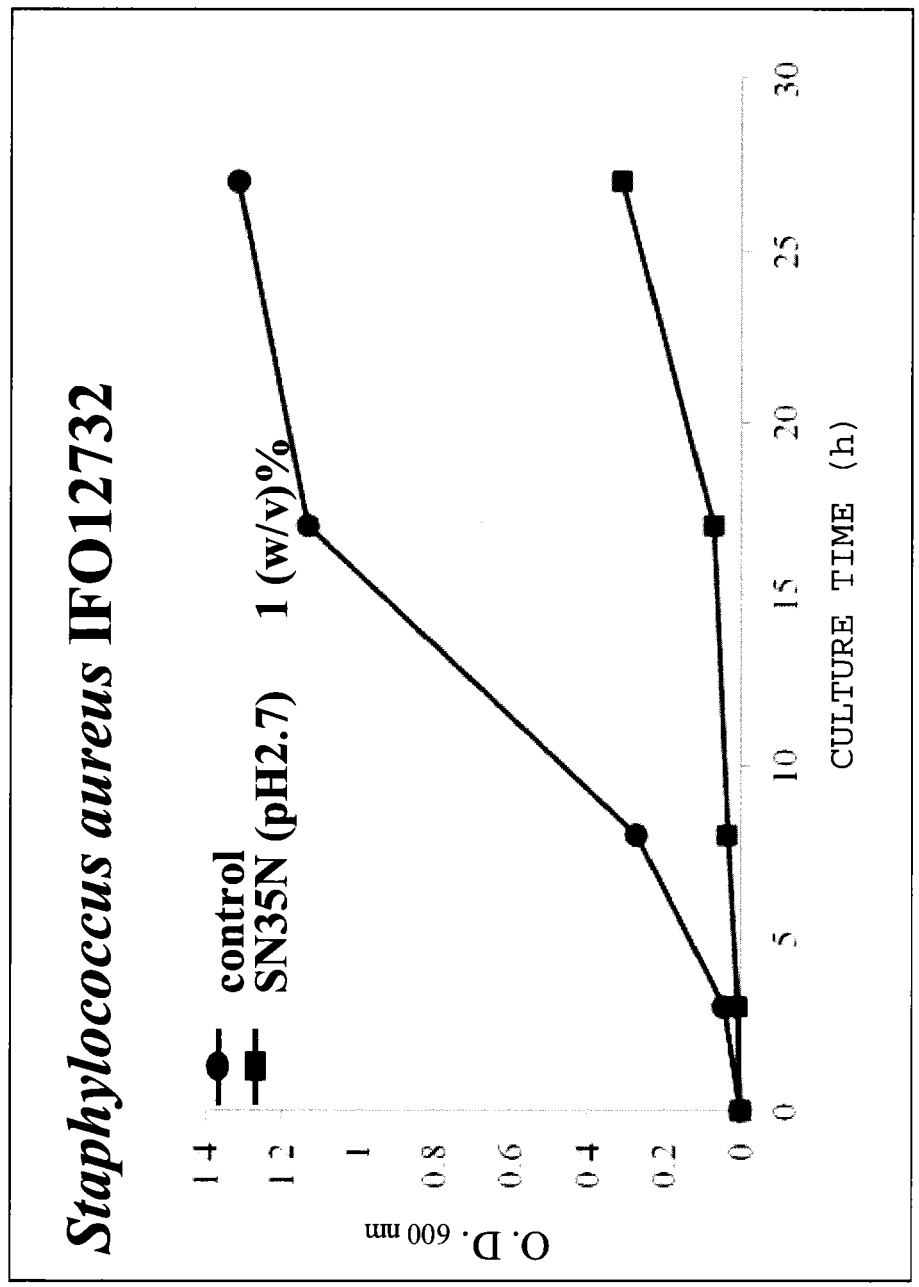
FIG. 8 is a graph showing the effect of the powdery malted rice extract composition (SN35N) on the growth of *Staphylococcus aureus*.
Figure 9:
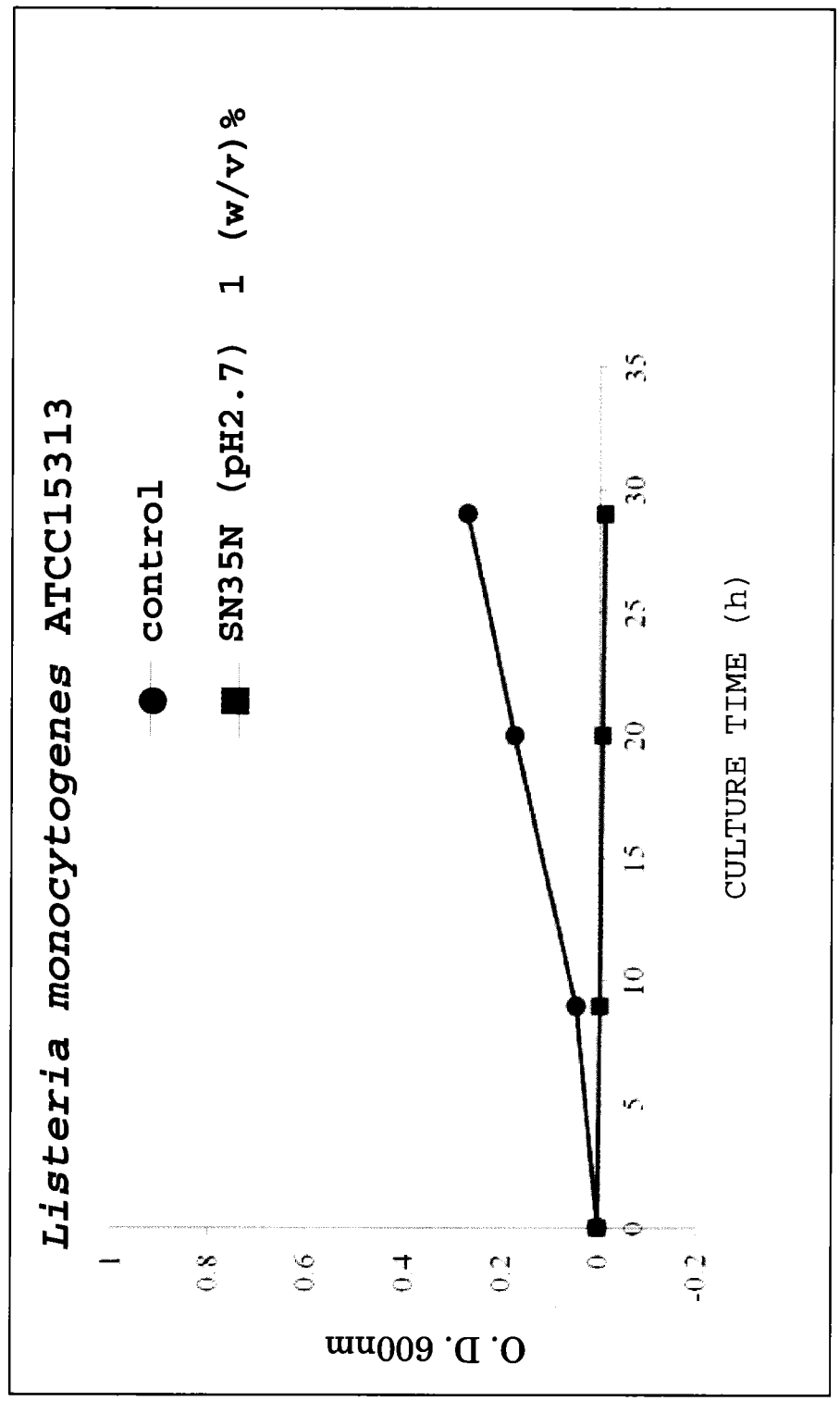
FIG. 9 is a graph showing the effect of the powdery malted rice extract composition (SN35N) on the growth of *Listeria monocytogenes*.

As shown in FIG. 2, proliferation of harmful bacteria was observed with sake lees, whereas no proliferation of harmful bacteria was observed with either the powdery malted rice extract composition 1 or the powdery malted rice extract composition 3. That is, the powdery malted rice extract composition of the present invention allows proliferation of lactic acid bacteria, particularly plant-derived lactic acid bacteria with slow proliferation ability, while inhibiting proliferation of harmful bacteria. Thus, the powdery malted rice extract composition of the present invention is assumed to be highly utilizable in the field of food industry. Because it suppresses the proliferation of harmful bacteria such as *Staphylococcus aureus*, it is highly anticipated to suppress also the proliferation of bacteria causing serious infectious diseases such as bacteria resistant against various antibiotics (multi-drug resistant bacteria) as typified by methicillin resistant *Staphylococcus aureus* (MRSA).

Example 4

Proliferation Promotion Test of Harmful Bacteria (2)

As the harmful bacteria, the *Enterococcus faecalis* IFO12964, *Escherichia coli* DH5α, *Bacillus subtilis* ATCC6633, *Bacillus cereus* ATCC11778, *Staphylococcus epidermidis* NBRC12993, and *Listeria monocytogenes* ATCC15313 strains were used. Further, using the *Staphylococcus aureus* IFO 12732 strain similarly to Example 3, a test was also performed in a similar manner to each of the above bacteria under the following conditions.

In a similar manner to Example 1, the powdery malted rice extract composition (SN35N (pH 2.7)) produced by inoculating and culturing (pH 2.7) the *Lb. plantarum* SN35N strain in the malted rice water extract solution was used as a sample. It was added to each of the following media in an amount of 1.0% (m/v) to prepare media: a Luria Broth (LB) medium (the product of Sigma-Aldrich Japan K.K.), which was used for *Escherichia coli*, the genus *Bacillus*, and the genus *Staphylococcus*; an MRS medium, which was used for the genus *Enterococcus* and the genus *Lactobacillus*; and a TY medium (3 (W/V) % triptic soya broth and 0.3 (W/v) % yeast extract), which was used for the genus *Listeria*. Then, each of the above bacterial strains was inoculated into corresponding medium and cultured at 37° C., and a bacterial turbidity was measured (OD 600 nm) every six hours. A medium containing none of the above substances was used as a control.

As shown in FIGS. 3 to 9, a proliferation inhibiting action on harmful bacteria was observed with the powdery malted rice extract composition of the present invention. This powdery malted rice extract composition is considered to be applicable as a preservative for food products and cosmetics.

Example 5

Proliferation Promotion Test of Plant-Derived Lactic Acid Bacteria (2)

As the plant-derived lactic acid bacteria, the aforementioned *Lb. plantarum* SN13T strain was used.

The powdery malted rice extract compositions (SN13T (pH 2.7), SN13T (pH 5.3), SN35N (pH 2.7), and SN35N (pH 5.3)) obtained by inoculating and culturing each of the *Lb. plantarum* SN13T and *Lb. plantarum* SN35N strains (pH 2.7 and pH 5.3) in a similar manner to Example 1 were used as samples. The samples were each added to MRS media in an amount of 0.75% (m/v) to prepare respective media. Then, the aforementioned plant-derived lactic acid bacteria strains were inoculated into each medium and cultured at 37° C., and a bacterial turbidity was measured (OD 600 nm) every six hours. A medium containing none of the above substances was used as a control.

Figure 10:
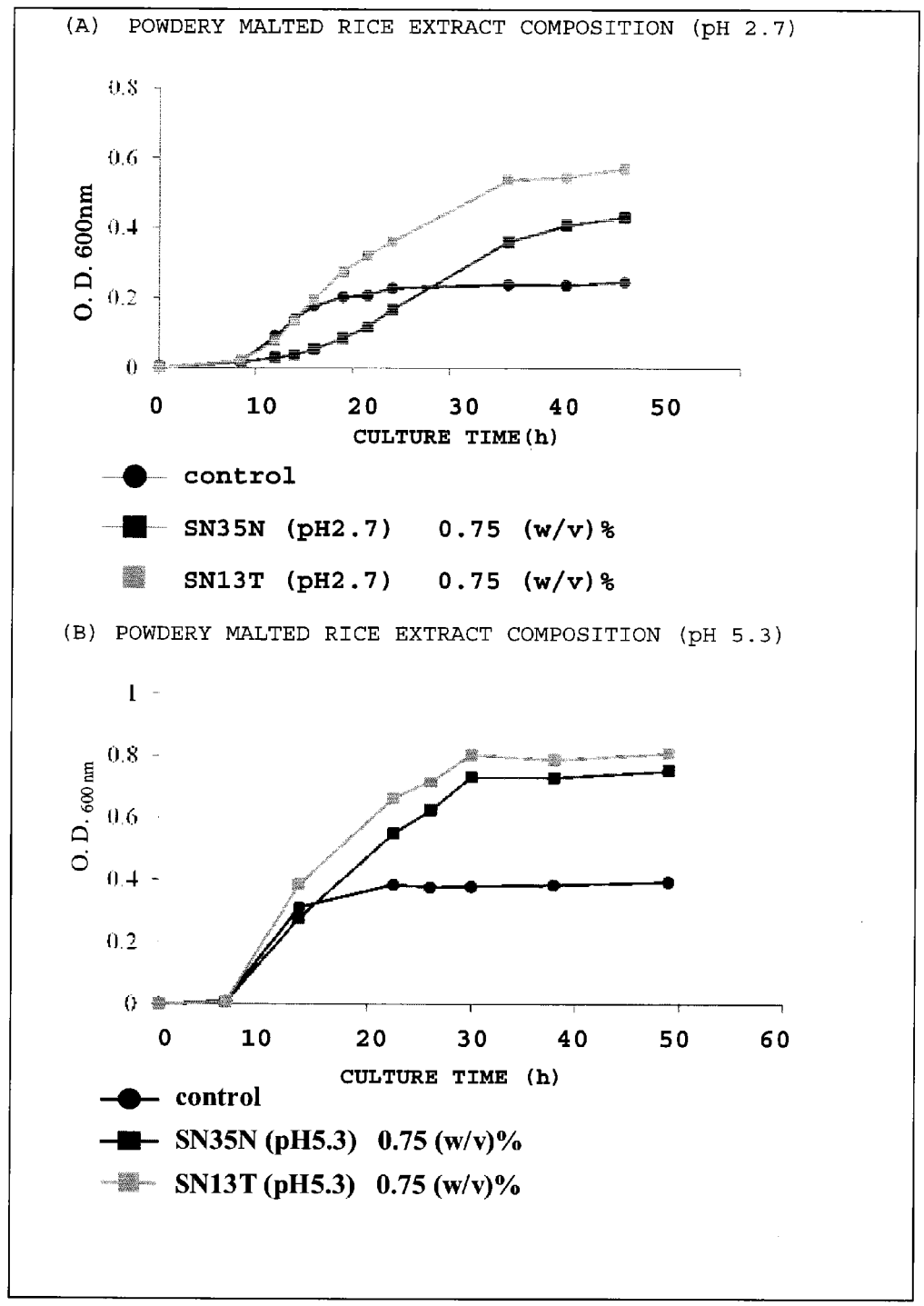
FIG. 10 is a graph showing the proliferation promoting effect of the powdery malted rice extract composition on plant-derived lactic acid bacteria ((A): the powdery malted rice extract composition (pH 2.7) and (B): the powdery malted rice extract composition (pH 5.3)).

As shown in FIG. 10, a proliferation promoting action on plant-derived lactic acid bacteria was observed with the powdery malted rice extract composition of the present invention, and it was shown that this action was enhanced to a greater degree with the composition prepared by inoculating lactic acid bacteria at pH 5 to 6.

The invention claimed is:

1. A powdery malted rice extract composition, obtained by a process comprising:
    inoculating lactic acid bacteria in a liquid prepared from a water extract of malted rice so that its Brix degree is from 0.01 to 10,
    culturing the bacteria in the liquid to obtain a culture, and subsequently drying the culture.

2. The composition of claim 1, wherein the malted rice is a culture product of yellow koji mold.

3. An agent, comprising: the composition of claim 1, wherein the agent is capable of promoting proliferation of plant-derived lactic acid bacteria.

4. A preservative, comprising: the composition of claim 1.

5. A composition comprising: the preservative of claim 4, and a cosmetic material, mixed with the preservative.

6. A fermented milk, produced by a process comprising:
    fermenting milk with plant-derived lactic acid bacteria in the presence of the composition of claim 1.

7. The composition of claim 1, wherein the Brix degree is from 0.5 to 5.

8. The composition of claim 1, wherein the culturing further comprises adjusting a pH of the liquid to from 5 to 8 by adding a pH adjuster.

9. The composition of claim 1, wherein the drying comprises freeze drying, cold air drying, or both.

10. A process, comprising: mixing the preservative of claim 4 with a cosmetic material.

11. A method for producing a fermented food product, comprising:
    fermenting milk, fruit juice, or plant juice with plant-derived lactic acid bacteria in the presence of the composition of claim 1.

12. A method for promoting proliferation of plant-derived lactic acid bacteria, the method comprising: contacting plant-derived lactic acid bacteria with the composition of claim 1 and culture media to promote proliferation and culturing the resultant mixture.

13. A method for preserving a cosmetic material or food product from decay, the method comprising: contacting a cosmetic material or food product with the composition of claim 1.

14. A method for producing a powdery malted rice extract composition, the method comprising:
   inoculating lactic acid bacteria in a liquid prepared from a water extract of malted rice so that its Brix degree is from 0.01 to 10,
   culturing the bacteria in the liquid to obtain a culture, and subsequently drying the culture.

15. The method of claim 14, wherein the liquid is produced by combining malted rice and an aqueous solution, and the resulting solution is incubated at from 30 to 70 degrees Celsius for from 1 minute to 48 hours.

16. The method of claim 14, wherein the process comprising preparing a water extract comprises preparing a water extract of malted rice so that its Brix degree is from 0.5 to 5.

17. The method of claim 14, wherein the culturing comprises adjusting a pH of the liquid to from 5 to 8 with addition of a pH adjuster.

18. The method of claim 14, wherein the drying comprises freeze drying, cold air drying, or both.

* * * * *